United States Patent
Fukuda et al.

(10) Patent No.: US 10,001,439 B2
(45) Date of Patent: Jun. 19, 2018

(54) LOCALIZED SURFACE PLASMON RESONANCE SENSING CHIP AND LOCALIZED SURFACE PLASMON RESONANCE SENSING SYSTEM

(71) Applicant: National Institute of Advanced Industrial Science and Technology, Tokyo (JP)

(72) Inventors: Takashi Fukuda, Tsukuba (JP); Akira Emoto, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days. days.

(21) Appl. No.: 15/500,396

(22) PCT Filed: Jul. 31, 2015

(86) PCT No.: PCT/JP2015/071866
§ 371 (c)(1),
(2) Date: Jan. 30, 2017

(87) PCT Pub. No.: WO2016/021516
PCT Pub. Date: Feb. 11, 2016

(65) Prior Publication Data
US 2017/0219488 A1    Aug. 3, 2017

(30) Foreign Application Priority Data
Aug. 4, 2014 (JP) ................................ 2014-158793

(51) Int. Cl.
*G01N 21/55* (2014.01)
*G01N 21/552* (2014.01)
*G02B 5/00* (2006.01)

(52) U.S. Cl.
CPC .......... *G01N 21/554* (2013.01); *G01N 21/55* (2013.01); *G01N 21/553* (2013.01); *G02B 5/008* (2013.01)

(58) Field of Classification Search
CPC .... G01N 21/553; G01N 21/55; G01N 21/554; G01N 21/474; G01N 21/57; H01B 1/22;
(Continued)

(56) References Cited

U.S. PATENT DOCUMENTS 6,476,901 B2 * 11/2002 Fujioka ................. G02F 1/1345
349/149
8,458,900 B2 * 6/2013 Kodani ............... H01L 21/4853
29/832

(Continued)

FOREIGN PATENT DOCUMENTS

JP    2009-85724 A    4/2009
JP    2011506916 A    3/2011
(Continued)

OTHER PUBLICATIONS

International Search Report for PCT Serial No. PCT/JP2015/071866 dated Oct. 6, 2015.
(Continued)

*Primary Examiner* — Tarifur Chowdhury
*Assistant Examiner* — Md M Rahman
(74) *Attorney, Agent, or Firm* — McCormick, Paulding & Huber LLP

(57) ABSTRACT

There are provided a localized surface plasmon resonance sensing chip in which a linewidth of an absorption spectrum originating from localized plasmon resonance is narrow and with which a peak wavelength shift of an optical spectrum accompanying a change in refractive index of a surface can be accurately measured, and a localized surface plasmon resonance sensing system using this sensing chip. A sensing
(Continued)

chip 10 includes a base 14 having a flat-plate shape, a plurality of protruding portions 16, and a metal layer 18 covering each front surface of the plurality of protruding portions 16. The protruding portions 16 each have a shape like a semi-oblate spheroid which is one of three-dimensional parts obtained by dividing an oblate spheroid in half along an equatorial plane and are arranged such that a divided surface 16*a* of the semi-oblate spheroid faces a front surface 14*a* of the base 14. A sensing system includes the sensing chip 10, a light source irradiating a detection region of the sensing chip 10 with light, and a photodetector detecting the optical spectrum of light emitted from the light source and then reflected in or transmitted through the detection region of the sensing chip 10.

20 Claims, 9 Drawing Sheets

(58) Field of Classification Search
CPC .......... H01B 1/16; H05K 1/092; H05K 1/095; C03C 8/18
USPC .......................................... 356/445; 252/514
See application file for complete search history.

(56) References Cited

U.S. PATENT DOCUMENTS

| 2009/0122310 | A1 | 5/2009 | Zhang et al. |
| 2010/0263923 | A1* | 10/2010 | Kodani ............... H01L 21/4853 174/260 |
| 2011/0164252 | A1 | 7/2011 | Handa et al. |
| 2013/0003070 | A1 | 1/2013 | Sezaki et al. |
| 2014/0154789 | A1 | 6/2014 | Polwart et al. |

FOREIGN PATENT DOCUMENTS

| JP | 2014-48083 A | 3/2014 |
| JP | 2014-514547 A | 6/2014 |
| WO | 2011/121857 A1 | 10/2011 |

OTHER PUBLICATIONS

Takashi Fukuda et al., "Development of Ultracompact Bio-Sensing System That Can Be Wirelessly Operated with Smart Device", Kogyo Zairyo, Dec. 1, 2013, vol. 61, No. 12, pp. 39 to 42.

* cited by examiner

LOCALIZED SURFACE PLASMON RESONANCE SENSING CHIP AND LOCALIZED SURFACE PLASMON RESONANCE SENSING SYSTEM

CROSS-REFERENCE TO RELATED APPLICATION

This application is a National Stage application of International Patent Application No. PCT/JP2015/071866, filed on Jul. 31, 2015, which claims priority to Japanese Patent Application Number 2014-158793, filed on Aug. 4, 2014, each of which is hereby incorporated by reference in its entirety.

TECHNICAL FIELD

The present invention relates to a highly sensitive sensing chip using localized surface plasmon resonance and a sensing system using this sensing chip.

BACKGROUND ART

A highly sensitive localized surface plasmon resonance sensor chip is known (International Publication No. WO 2011/121857). The chip described in International Publication No. WO 2011/121857 has higher sensitivity than conventional ones. However, since an absorption spectrum originating from localized plasmon resonance has a relatively broad linewidth, some contrivance is required for this chip to detect minute spectral shifts. For this reason, in some cases, the absorption spectrum of a chip is accurately measured by a spectral photometer having high wavelength resolution, and a spectral shift before and after sensing is analyzed based on a technique such as peak fitting. It is very difficult to measure spectra by using conventional tabletop-size spectral photometers at a bedside, a clinical site, an airport and a seaport, or a region without a sufficient social infrastructure. There has been a demand for the advent of a sensing chip and a sensing system which can accurately and easily measure the peak wavelength shift of an optical spectrum in any places.

SUMMARY

The present invention is achieved in view of these matters, and an object of the present invention is to provide a localized surface plasmon resonance sensing chip in which the linewidth of an absorption spectrum originating from localized plasmon resonance is narrow and with which a peak wavelength shift of an optical spectrum accompanying a change in refractive index of a surface can be measured with high accuracy, and a localized surface plasmon resonance sensing system using this sensing chip.

A localized surface plasmon resonance sensing chip of a first mode of the present invention includes: a base having a flat-plate shape; a plurality of protruding portions each having a shape like a semi-oblate spheroid which is one of three-dimensional parts obtained by dividing an oblate spheroid in half along an equatorial plane and arranged such that a divided surface of the semi-oblate spheroid faces a front surface of the base; and a metal layer covering each front surface of the plurality of protruding portions. The plurality of protruding portions are arranged at predetermined pitches in a diametrical direction of the divided surface and a direction perpendicular to the diametrical direction, respectively. Preferably, a ratio H/D of a height H of the protruding portion to a diameter D of the divided surface is not less than 0.1 and less than 0.5.

A localized surface plasmon resonance sensing chip of a second mode of the present invention includes: a base having a flat-plate shape; a plurality of protruding portions each having a shape like a semi-prolate spheroid which is one of three-dimensional parts obtained by dividing a prolate spheroid in half along a direction perpendicular to an equatorial plane and arranged such that a divided surface of the semi-prolate spheroid faces a front surface of the base; and a metal layer covering each front surface of the plurality of protruding portions. The plurality of protruding portions are arranged at predetermined pitches in a longitudinal direction of the divided surface and a direction perpendicular to the longitudinal direction, respectively, with longitudinal directions of the divided surfaces being parallel to each other. Preferably, a ratio H/A of a height H of the protruding portion to a length A of the divided surface in the longitudinal direction is not less than 0.1 and less than 0.5.

A localized surface plasmon resonance sensing chip of a third mode of the present invention includes: a base having a flat-plate shape; a plurality of protruding portions each having a shape like one of three-dimensional parts obtained by dividing a prolate spheroid in half along an equatorial plane and arranged such that a divided surface of the three-dimensional part faces a front surface of the base; and a metal layer covering each front surface of the plurality of protruding portions. The plurality of protruding portions are arranged at predetermined pitches in a diametrical direction of the divided surface and a direction perpendicular to the diametrical direction, respectively. Preferably, a ratio H/D of a height H of the protruding portion to a diameter D of the divided surface is more than 0.5 and not more than 6.

A localized surface plasmon resonance sensing chip of a fourth mode of the present invention includes: a base having a flat-plate shape; a plurality of protruding portions each having a shape like a shape of a three-dimensional part obtained by stretching one of parts, obtained by dividing a prolate spheroid in half along an equatorial plane, from both sides in a diametrical direction of the equatorial plane so as to have an elliptic bottom surface and arranged such that a divided surface of the three-dimensional part faces a front surface of the base; and a metal layer covering each front surface of the plurality of protruding portions. The plurality of protruding portions are arranged at predetermined pitches in a longitudinal direction of the divided surface and a direction perpendicular to the longitudinal direction, respectively, with longitudinal directions of the divided surfaces being parallel to each other. Preferably, a ratio H/A of a height H of the protruding portion to a length A of the divided surface in the longitudinal direction is more than 0.5 and not more than 6.

In the localized surface plasmon resonance sensing chip of the present invention, a thickness of the metal layer is preferably 10 nm to 200 nm. In addition, in the localized surface plasmon resonance sensing chip of the present invention, each of the pitches is preferably 100 nm to 3,000 nm.

In addition, in the localized surface plasmon resonance sensing chip of the present invention, the metal layer is preferably made of Au, Pt, Ag, Al, or an alloy thereof. In addition, in the localized surface plasmon resonance sensing chip of the present invention, the plurality of protruding portions are preferably closely packed. In addition, in the localized surface plasmon resonance sensing chip of the present invention, an organic molecular layer for fixing a biomolecule may further be formed on a front surface of the metal layer.

A localized surface plasmon resonance sensing system of a first mode of the present invention includes: a localized surface plasmon resonance sensing chip of the present invention; a light source irradiating a detection region of the localized surface plasmon resonance sensing chip with light; and a photodetector detecting an optical spectrum of light emitted from the light source and then reflected in or transmitted through the detection region of the localized surface plasmon resonance sensing chip. A wireless communication device wirelessly transmitting data of an optical spectrum detected by the photodetector, and a portable terminal receiving the data wirelessly transmitted from the wireless communication device and quantitatively evaluating adsorption of a detection substance to the localized surface plasmon resonance sensing chip based on the data may further be included.

A localized surface plasmon resonance sensing system of a second mode of the present invention includes: a localized surface plasmon resonance sensing chip of the present invention; a light source irradiating a detection region of the localized surface plasmon resonance sensing chip with light; a shooting device shooting the detection region of the localized surface plasmon resonance sensing chip; and an evaluation device quantitatively evaluating adsorption of a detection substance to the localized surface plasmon resonance sensing chip based on chromaticity of an image of the detection region shot by the shooting device. A wireless communication device wirelessly transmitting, to a remote sever, data of the chromaticity of the image and/or data of an adsorption amount of the detection substance may further be included.

According to the present invention, it is possible to obtain a localized surface plasmon resonance sensing chip in which the linewidth of an absorption spectrum originating from localized plasmon resonance is narrow and with which a peak wavelength shift of an optical spectrum accompanying a change in refractive index of a surface can be measured with high accuracy, and a localized surface plasmon resonance sensing system using this sensing chip.

BRIEF DESCRIPTIONS OF THE DRAWINGS

Figure 6:
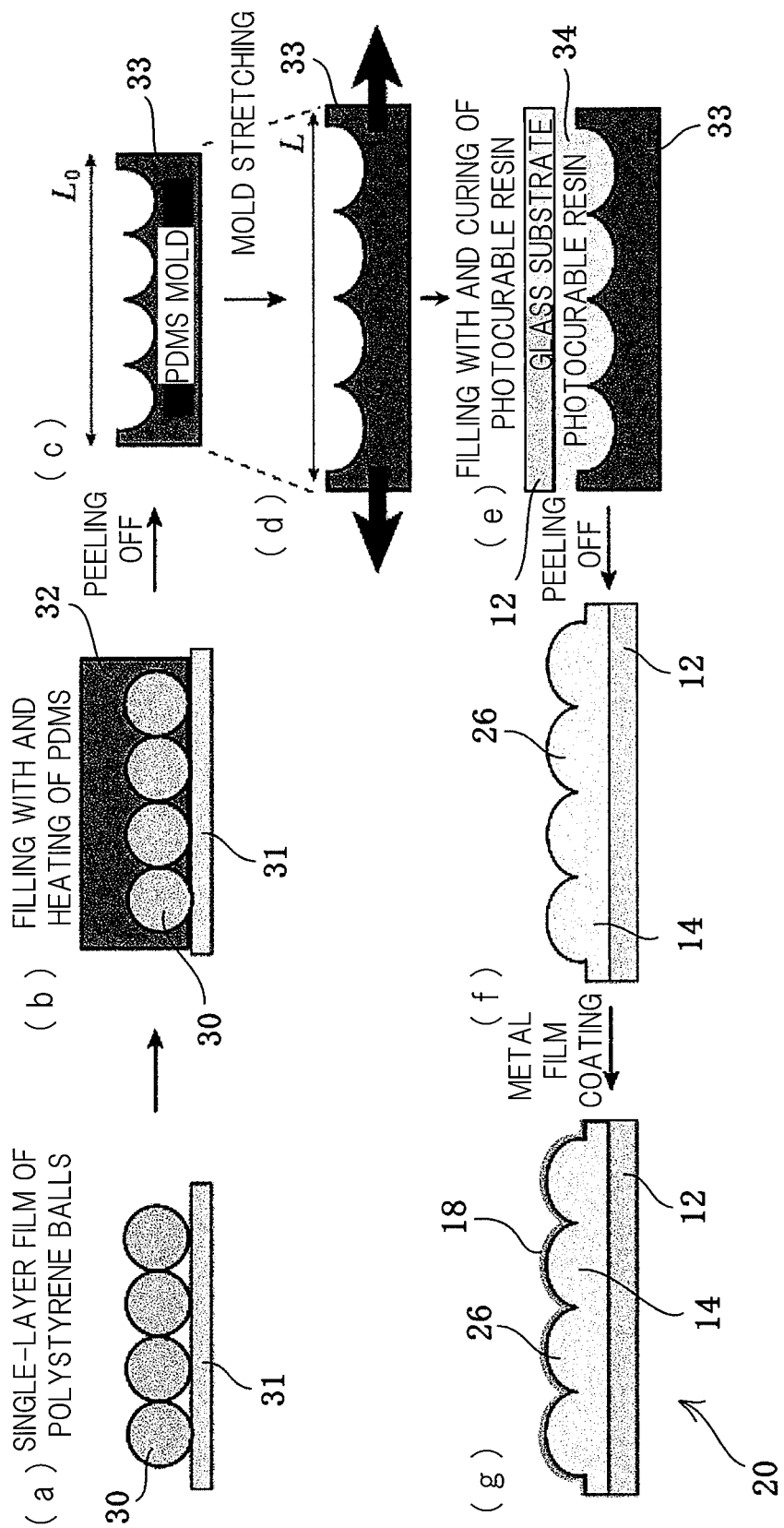
Figure 7:
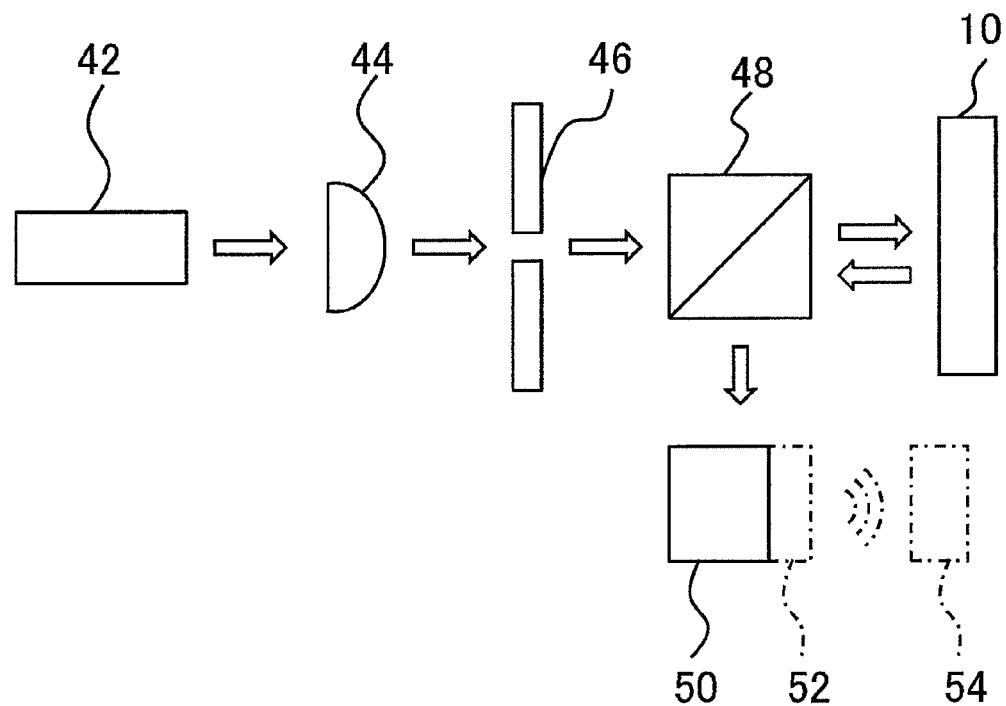
Figure 8:
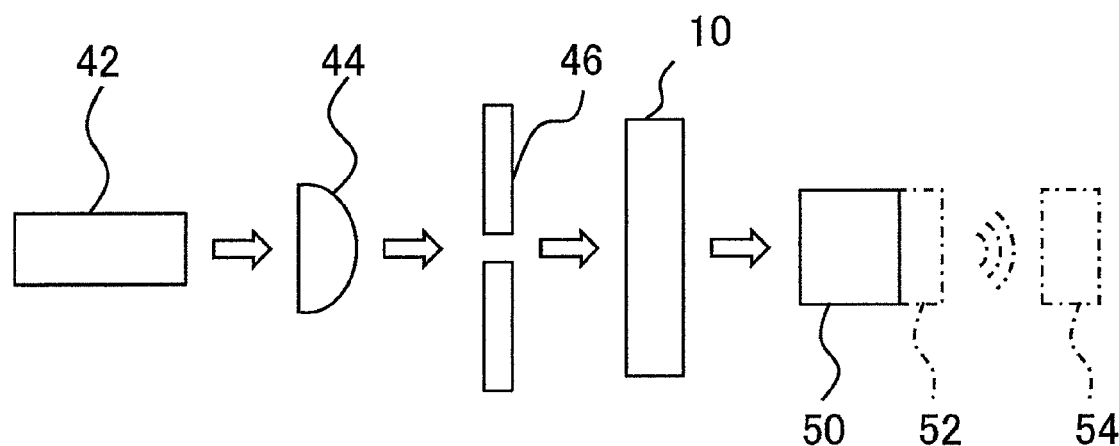
Figure 9:
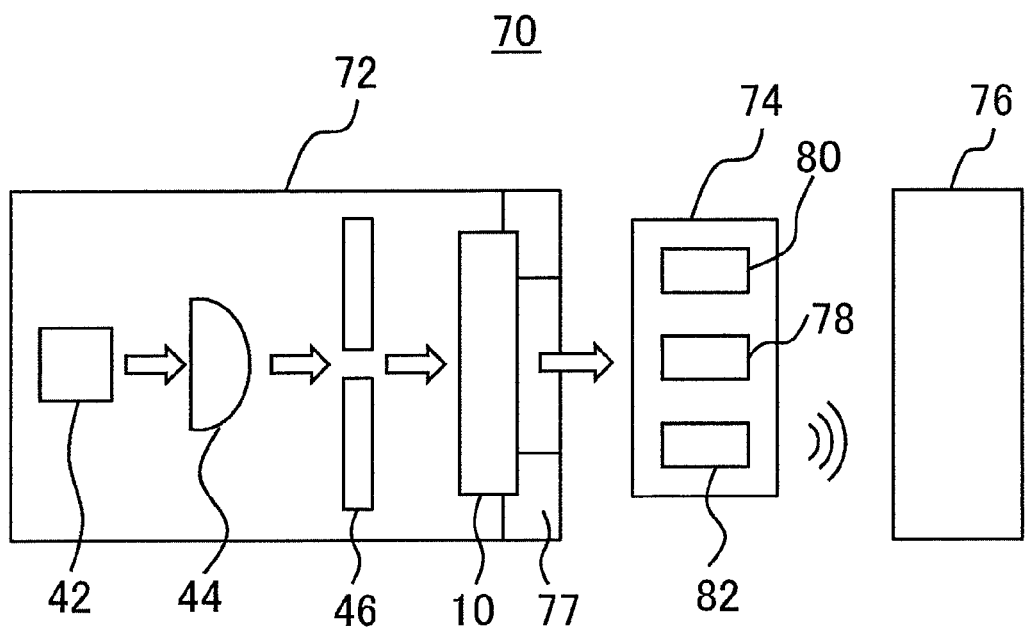
Figure 10:
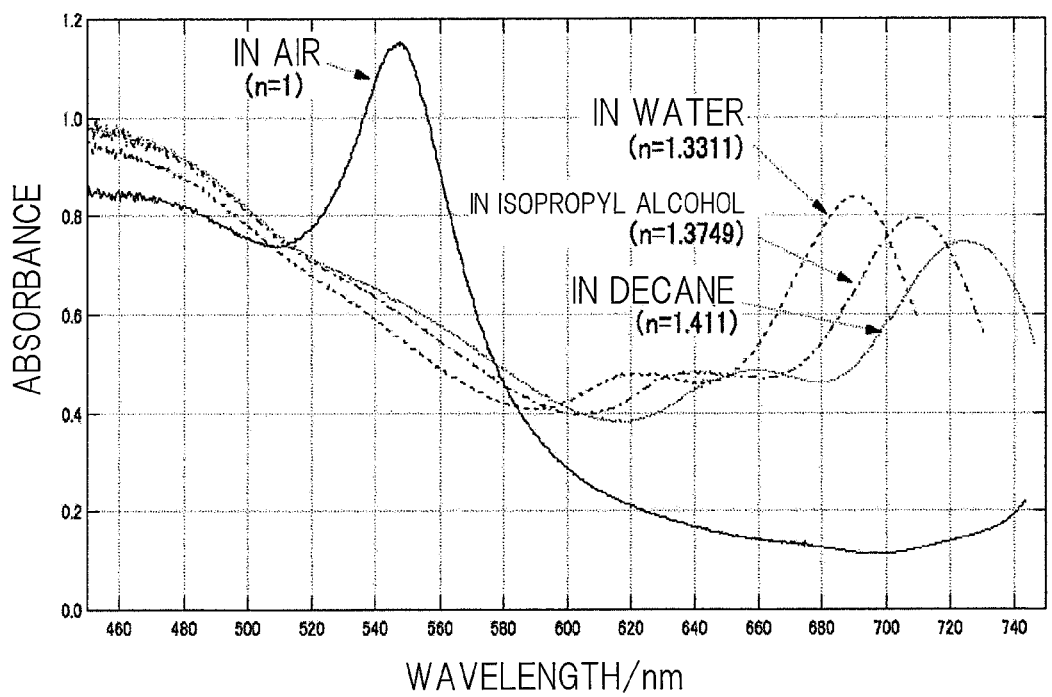
Figure 11:
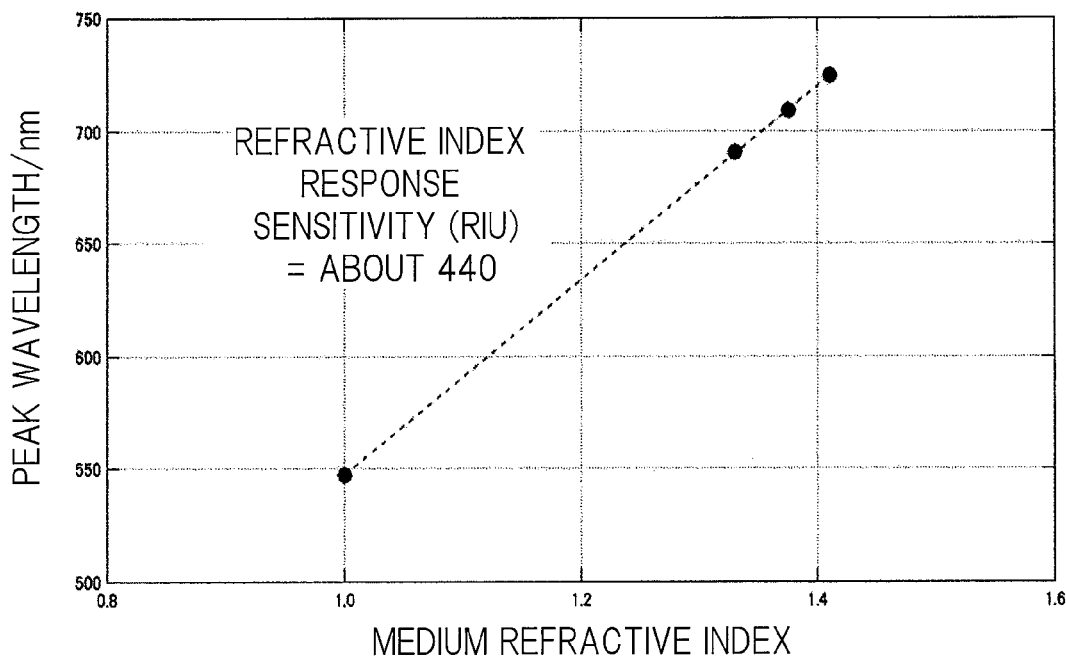
Figure 12:
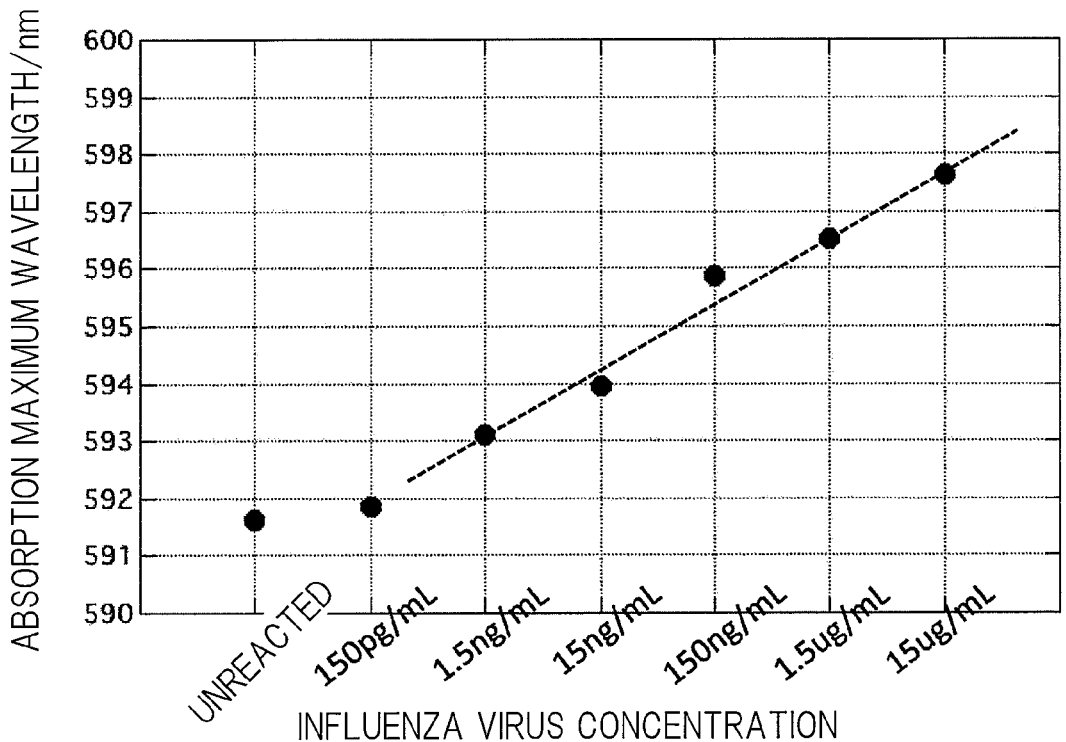
Figure 13:
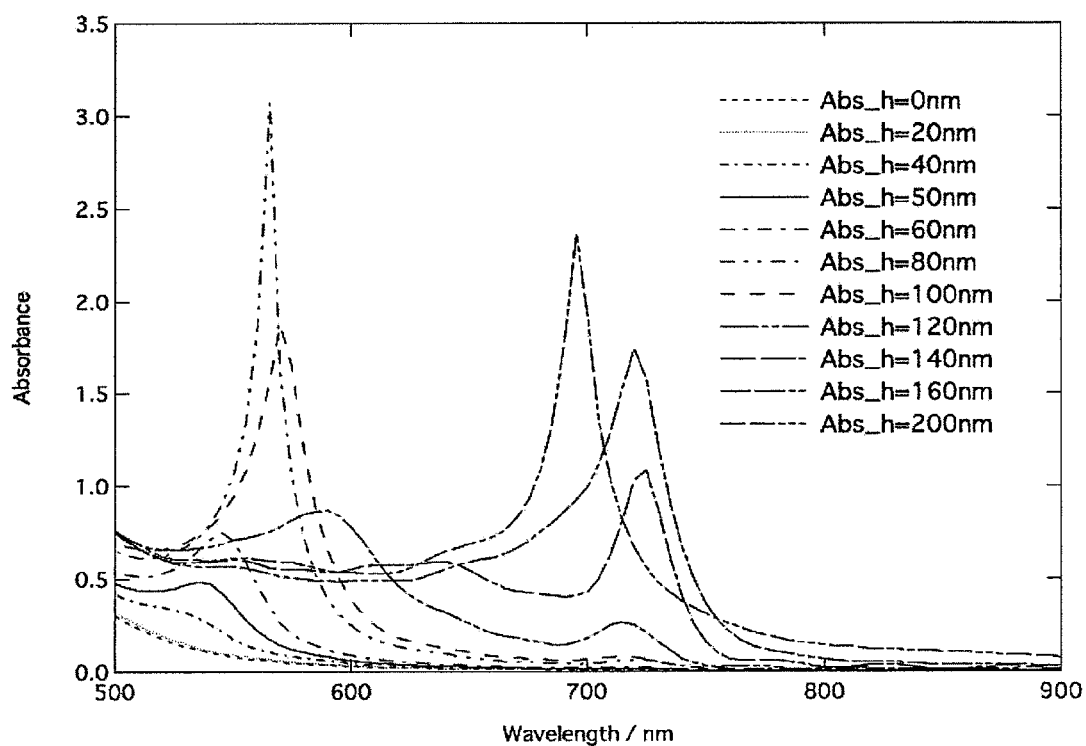
Figure 14:
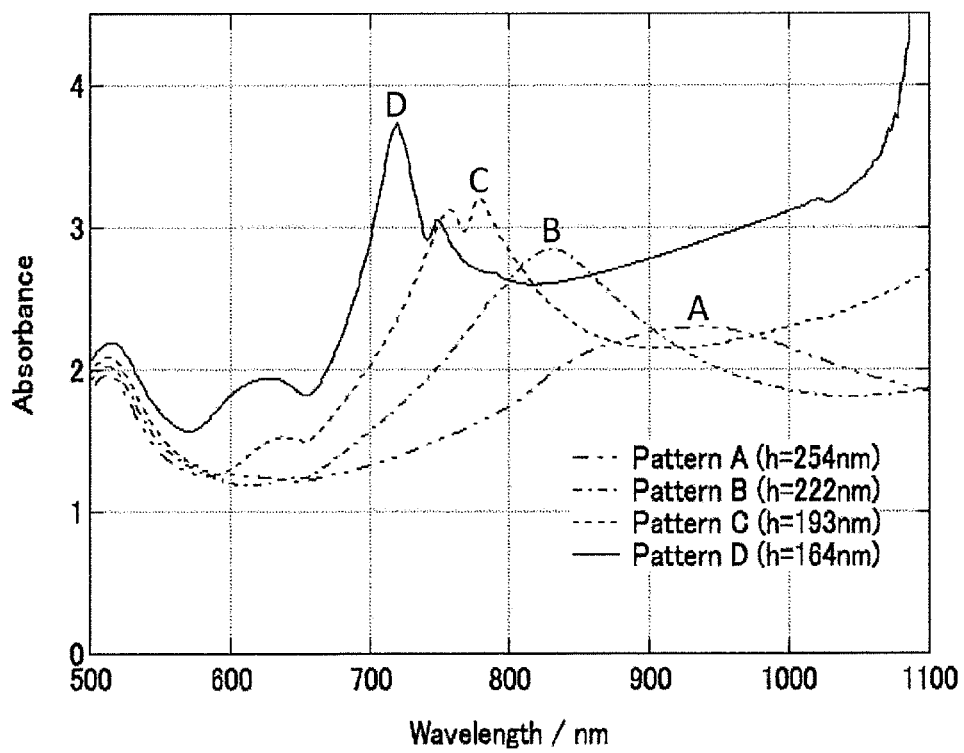
Figure 15:
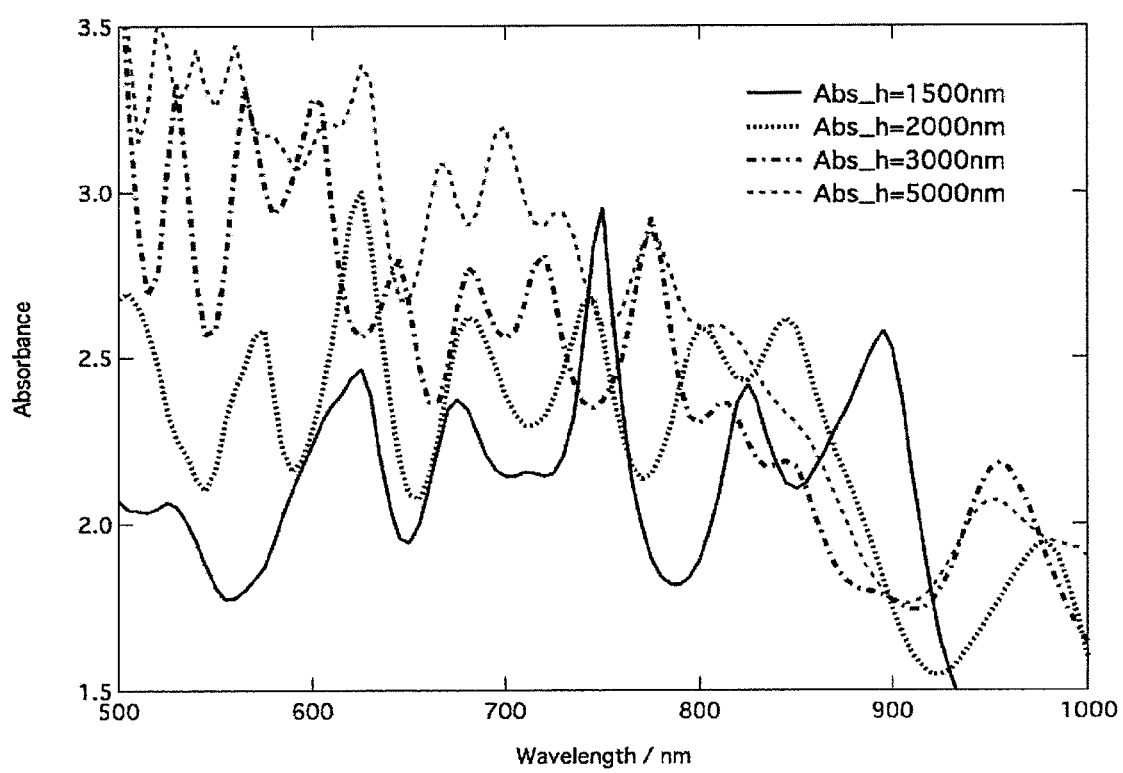

FIGS. 6 (a) to (g) show schematic cross-sectional views for describing a method of manufacturing the localized surface plasmon resonance sensing chip according to the second embodiment of the present invention;

FIG. 7 is a view for describing a configuration of a reflective localized surface plasmon resonance sensing system according to the present invention;

FIG. 8 is a view for describing a configuration of a transmissive localized surface plasmon resonance sensing system according to the present invention;

FIG. 9 is a view for describing a configuration of a portable localized surface plasmon resonance sensing system according to the present invention;

FIG. 10 is a graph showing optical spectra of the localized surface plasmon resonance sensing chip according to the second embodiment of the present invention in various types of media;

FIG. 11 is a graph showing a relation between refractive indices of a liquid dropped on the localized surface plasmon resonance sensing chip according to the second embodiment of the present invention and peak wavelengths of the optical spectra;

FIG. 12 is a graph showing a relation between concentrations of solutions of a test substance applied to the localized surface plasmon resonance sensing chip according to the second embodiment of the present invention and the peak wavelengths of the optical spectra;

FIG. 13 is a graph showing the optical spectra of the localized surface plasmon resonance sensing chip according to the first embodiment of the present invention, obtained by performing simulations for the respective heights of protruding portions;

FIG. 14 is a graph showing the optical spectra of the localized surface plasmon resonance sensing chips according to the first embodiment and a third embodiment of the present invention, obtained by performing simulations for the respective heights of protruding portions; and FIG. 15 is a graph showing the optical spectra of the localized surface plasmon resonance sensing chip according to the third embodiment of the present invention, obtained by performing simulations for the respective heights of the protruding portions.

DETAILED DESCRIPTION

A localized surface plasmon resonance sensing chip (sometimes simply referred to as a "sensing chip" hereinafter) according to the present invention and a localized surface plasmon resonance sensing system (to be sometimes simply referred to as a "sensing system" hereinafter) using this sensing chip will be described below based on embodiments and an example with reference to the accompanying drawings. Note that the accompanying drawings schematically show sensing chips, sensing systems, and their peripheral members, and actual dimensions and actual dimension ratios do not necessarily match the dimensions and the dimension ratios on the drawings. Repetitive descriptions will be omitted where appropriate, and the same reference characters may denote the same members. When expressing a numerical range by writing "to" between two numerical values, the range also includes the two numerical values.

(Sensing Chip According to First Embodiment)

Figure 1:
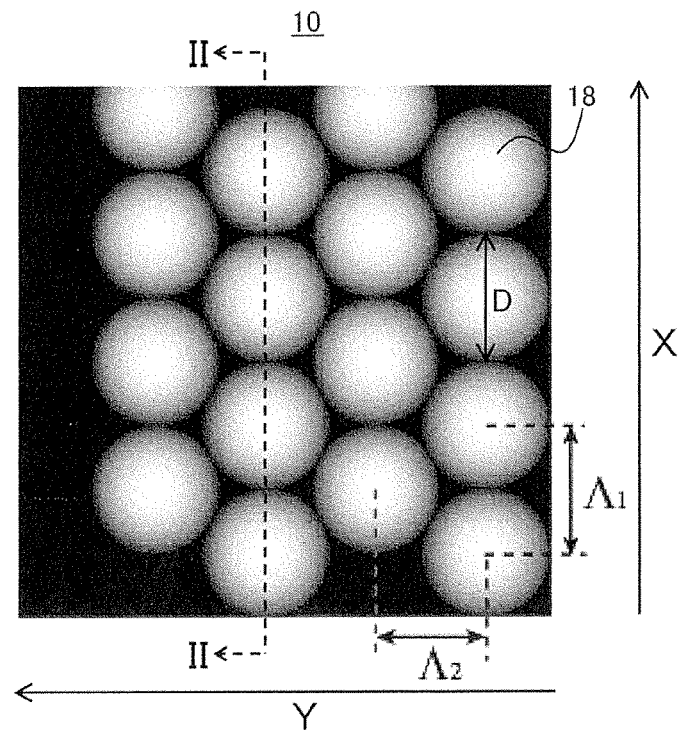
FIG. 1 is a plan view of a localized surface plasmon resonance sensing chip according to a first embodiment of the present invention.
Figure 2:
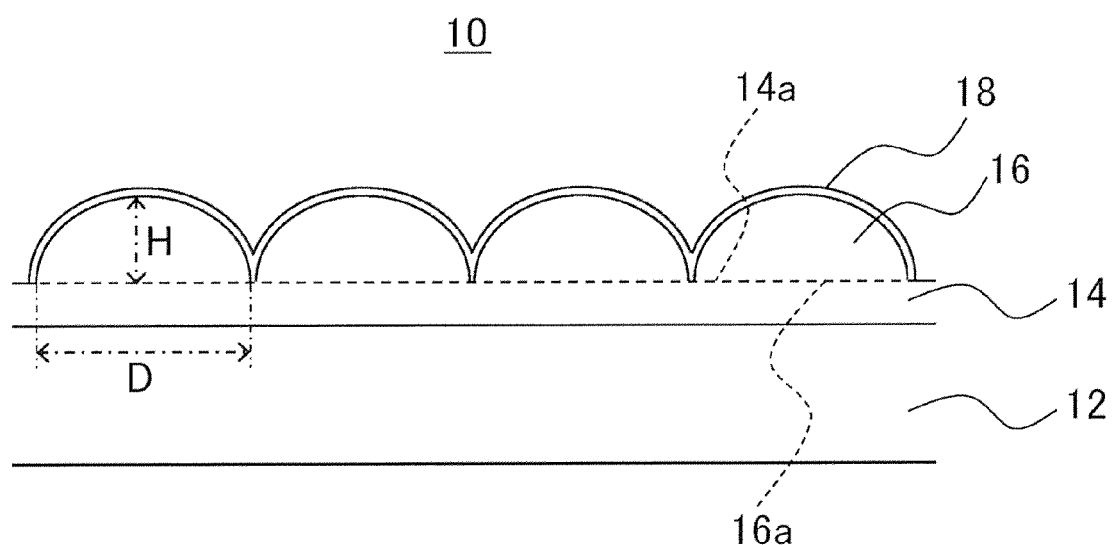
FIG. 2 is a schematic cross-sectional view of an end surface of a portion cut along a line II-II in FIG. 1.

FIG. 1 shows a three-dimensional shaded view of a sensing chip 10 according to the first embodiment of the present invention when viewed from above. FIG. 2 shows an end surface obtained by cutting the sensing chip 10 in FIG. 1 along a line II-II. As shown in FIGS. 1 and 2, the sensing chip 10 includes a substrate 12, a base 14, protruding portions 16, and a metal layer 18. The substrate 12 is made of glass and is used to form the base 14 and the protruding portions 16 in the manufacturing process for the sensing chip 10. A method of manufacturing the sensing chip 10 will be described later. The substrate 12 may be made of, for example, a thermoplastic resin such as a polyester resin, a polyolefin-based resin, a polystyrene resin, an ABS resin, a polyacetal resin, a polycarbonate resin, or a polyamide resin or a thermosetting resin such as a polyimide resin, a phenol resin, a melamine resin, or an epoxy resin. The base 14 has a flat-plate shape and is made of a resin.

Each protruding portion 16 is made of a resin and formed on the base 14. In this embodiment, the base 14 and the protruding portions 16 are integrally molded with a resin. However, the base 14 and the protruding portions 16 may be made of different materials or different members. The protruding portion 16 has a semi-oblate shape. A semi-oblate spheroid is a half of an oblate spheroid and one of three-dimensional parts obtained by dividing an oblate spheroid in half having the same size along the equatorial plane. An oblate spheroid is a spheroid with a short axis of an ellipse being a rotation axis. That is, an oblate spheroid is a spheroid with the short radius of the ellipse being the polar radius, and the long radius of the ellipse being the equatorial radius.

Each protruding portion 16 is disposed such that a divided surface 16a of the semi-oblate spheroid faces a front surface 14a of the base 14. That is, the protruding portion 16 is disposed on the base 14 in a shape obtained by pressing a hemisphere downward from above. Note that the divided surface 16a has a circular shape. In addition, as shown in FIG. 1, the protruding portions 16 are closely packed at predetermined pitches $\wedge_1$ and $\wedge_2$ in a direction X as one of diametrical directions of the divided surfaces 16a and a direction Y perpendicular to the direction X, respectively. In this embodiment, the protruding portions 16 are closely packed. However, they may be disposed in a lattice pattern. The pitches $\wedge_1$ and $\wedge_2$ are preferably 100 nm to 3,000 nm. The detection region of the sensing chip 10 resonates with light having wavelengths equivalent to pitches $\wedge_1$ and $\wedge_2$. This is because the range from the ultraviolet light wavelength region to the visible light wavelength region to the near-infrared light wavelength region to be used for detection corresponds to 100 nm to 3,000 nm.

Although described in detail in an example, each protruding portion 16 is preferably formed such that a ratio H/D of a height H of the protruding portion 16 to a diameter D of the divided surface 16a is equal to or more than 0.1 and less than 0.5. This is because, in the wavelength range of light used for detection (from ultraviolet light to visible light to near-infrared light), the peak wavelength of the optical spectrum of the sensing chip 10 is expected to clearly appear. The metal layer 18 covers each front surface of the protruding portions 16. The metal layer 18 is preferably made of Au, Pt, Ag, Al, or an alloy of them. This is because these metals can cause strong localized surface plasmon resonance.

The metal layer 18 preferably has a thickness of 10 nm to 200 nm in order to efficiently cause localized surface plasmon resonance and perform measurement with a light reflective or a light transmissive sensing system. If the metal layer 18 has a thickness of 10 nm or more, it is possible to obtain a sufficient amount of light reflected from the sensing chip 10 when using the sensing chip 10 for a light reflective sensing system. In addition, in a case in which the metal layer 18 has a thickness of 200 nm or less, when the sensing chip 10 is used for a light transmissive sensing system, it is possible to obtain a sufficient amount of light transmitted from the sensing chip 10. An organic molecular layer for fixing biomolecules may be further formed on the front surface of the metal layer 18. This allows the sensing chip 10 to be used as a biosensor which can detect a specific biomolecule.

(Sensing Chip According to Second Embodiment)

Figure 3:
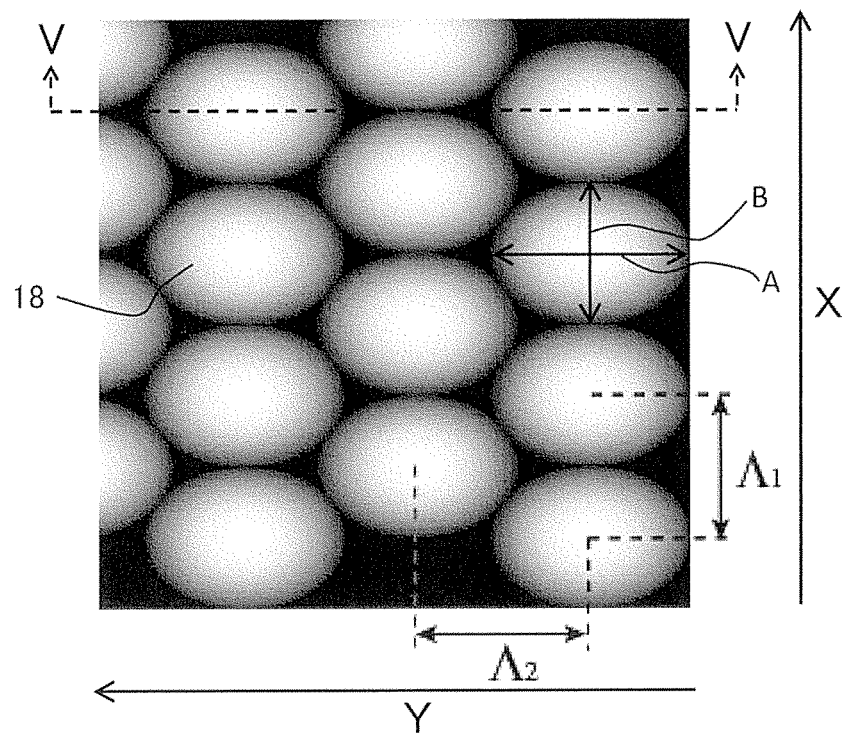
FIG. 3 is a plan view of a localized surface plasmon resonance sensing chip according to a second embodiment of the present invention.
Figure 4:
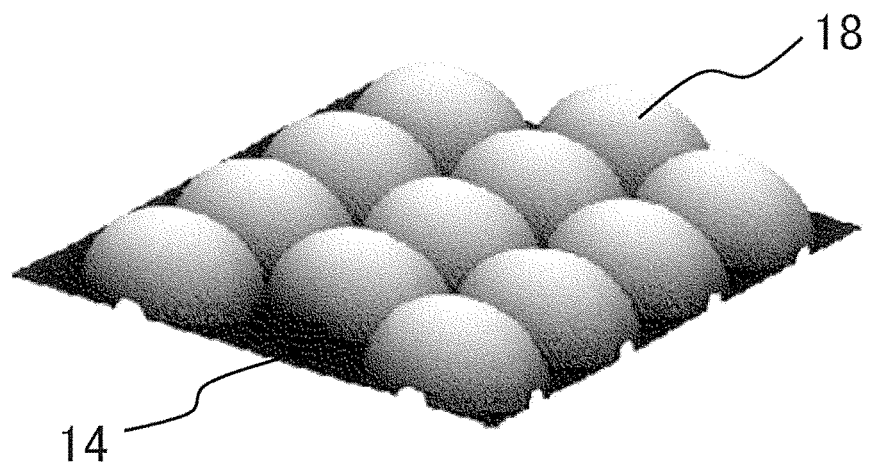
FIG. 4 is a perspective view of a localized surface plasmon resonance sensing chip according to the second embodiment of the present invention.
Figure 5:
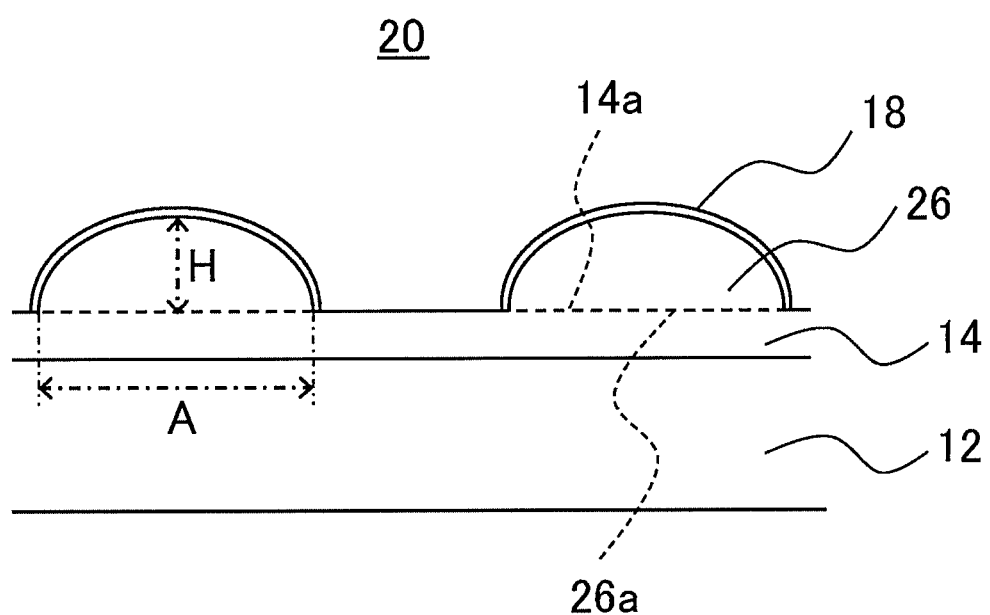
FIG. 5 is a schematic cross-sectional view of an end surface of a portion cut along a line V-V in FIG. 3.

FIG. 3 shows a state of a sensing chip 20 according to the second embodiment of the present invention when viewed from above. FIG. 4 shows a state of the sensing chip 20 when viewed obliquely from above. FIGS. 3 and 4 are three-dimensional shaded views. FIG. 5 shows an end surface obtained by cutting the sensing chip 20 in FIG. 3 along a line V-V. A shape and an arrangement of each protruding portion 26 of the sensing chip 20 differ from those of the protruding portions 16 of the sensing chip 10. A structure of the sensing chip 20 is the same as that of the sensing chip 10 except for the shape and the arrangement of each protruding portion 26.

Each protruding portion 26 has a shape like a semi-prolate spheroid. A semi-prolate spheroid is a half of a prolate spheroid and is one of three-dimensional parts obtained by dividing a prolate spheroid in half having the same size along a direction perpendicular to the equatorial plane. A divided surface 26a of the protruding portion 26 has an elliptic shape. A prolate spheroid is a spheroid with the long axis of an ellipse being a rotation axis. That is, a prolate spheroid is a spheroid with the long radius of the ellipse being the polar radius, and the short radius of the ellipse being the equatorial radius. As shown in FIG. 3, the protruding portions 26 are disposed at predetermined pitches $\wedge_1$ and $\wedge_2$ in a short axis direction X and a long axis direction Y, respectively, such that the long axis directions of the divided surfaces 26a are parallel to each other.

Each of the pitches $\wedge_1$ and $\wedge_2$ is preferably 100 nm to 3,000 nm. This is because the pitches $\wedge_1$ and $\wedge_2$ correspond to the range from the ultraviolet light wavelength region to the visible light wavelength region to the near-infrared light wavelength region, and the sensing chip 20 resonates with light in this range. Each protruding portion 26 is preferably formed such that a ratio H/A of a height H of the protruding portion 26 to a long-axis length of the divided surface 26a, i.e., a length A in the longitudinal direction, is equal to or more than 0.1 and less than 0.5. This is because the peak wavelength of the optical spectrum of the sensing chip 20 is considered to clearly shift in accordance with the presence/absence of a detection substance.

(Sensing Chip According to Third Embodiment)

A sensing chip according to the third embodiment of the present invention is obtained by increasing the height of each protruding portion 16 of the sensing chip 10. The sensing chip according to the third embodiment includes a base having a flat-plate shape, a plurality of protruding portions, and a metal layer. Each protruding portion has a shape like one of three-dimensional parts obtained by dividing a prolate spheroid into equal two parts along the equatorial plane. In addition, each protruding portion is disposed such that a divided surface of this three-dimensional part faces a front surface of the base. The metal layer covers each front surface of the plurality of protruding portions. Then, the plurality of protruding portions are disposed at predetermined pitches in the diametrical direction of each divided surface and a direction perpendicular to the diametrical direction, respectively. A ratio H/D of a height H of each protruding portion to a diameter D of each divided surface is preferably more than 0.5 and equal to or less than 6.

(Sensing Chip According to Fourth Embodiment)

A sensing chip according to the fourth embodiment of the present invention is obtained by increasing the height of each protruding portion 26 of the sensing chip 20. The sensing chip according to the fourth embodiment includes a base having a flat-plate shape, a plurality of protruding portions, and a metal layer. Each protruding portion has a shape like a three-dimensional part obtained by stretching one of parts, obtained by dividing a prolate spheroid in half along the equatorial plane, from both sides in the diametrical direction of the equatorial plane so as to have an elliptic bottom surface. In addition, each protruding portion is disposed such that a divided surface of this three-dimensional part faces a front surface of the base. The metal layer covers each front surface of the plurality of protruding portions. Then, the plurality of protruding portions are disposed at predetermined pitches in the longitudinal direction of each divided surface and a direction perpendicular to the longitudinal direction, respectively, such that the respective longitudinal directions are parallel to each other. A ratio H/A of a height H of each protruding portion to a length A of the divided surface in the longitudinal direction is preferably more than 0.5 and equal to or less than 6.

(Method of Manufacturing Sensing Chip According to Second Embodiment)

FIG. 6 shows a method of manufacturing the sensing chip 20. The sensing chip 20 is manufactured as follows. First, a glass substrate 31 is dipped in a colloid solution of commercially available polystyrene balls 30 each having a diameter of 500 nm. The glass substrate 31 may be replaced by a substrate made of a different material. A dip coater is then used to pull out the glass substrate 31 at an appropriate speed to closely pack the polystyrene balls 30 as a single-layer film, as shown in FIG. 6(a). At this time, the polystyrene balls 30 are arrayed at predetermined vertical and horizontal pitches (corresponding to $\Lambda_1$ and $\Lambda_2$ in FIG. 1). As shown in FIG. 6(b), the resultant structure is then filled with a silicone monomer 32, which is a liquid mold material (PDMS: SIM-360 manufactured by Shin-Etsu Chemical Co., Ltd) and heated to be cured.

Next, when the cured silicone rubber is peeled off from the closely packed structure of the polystyrene balls 30, a mold 33 having a hemispherical curved surface formed in its front surface is obtained, as shown in FIG. 6(c). As shown in FIG. 6(d), the mold 33 is then stretched in one direction. In this case, a ratio $L/L_0$ of a length L of the mold after stretching to a length $L_0$ of the mold before stretching is defined as a stretching degree. The stretching degree $L/L_0$ is equivalent to a ratio A/B of the long-axis length A to a short-axis length B of the divided surface 26a shown in FIG. 3. Next, as shown in FIG. 6(e), after the resultant structure is filled with an acrylic monomer 34 (NOA61 manufactured by Norland Products Inc.), which is a liquid mold material, the substrate 12 made of glass covers the resultant structure, which is then cured by irradiation with ultraviolet light. Note that the material for the substrate 12 may be a material other than glass as long as it transmits ultraviolet light.

Then, as shown in FIG. 6(f), when the mold 33 is peeled off from the cured resin, the base 14 and the protruding portions 26 are integrally formed. Next, as shown in FIG. 6(g), the front surfaces of the protruding portions 26 are coated with a metal film with a thickness of about 100 nm to form the metal layer 18. In this manner, the sensing chip 20 is obtained. The mold 33 is stretched in two orthogonal directions in the step shown in FIG. 6(d), and another step can be performed in the same manner as the method of manufacturing the sensing chip 20 to obtain the sensing chip 10 including the protruding portions 16 each having a shape like a semi-oblate shape. It is possible to form the protruding portions 16 and 26 of the sensing chips 10 and 20 or the protruding portions of the sensing chips according to the third and the fourth embodiments by a method other than this manufacturing method. For example, such protruding portions can be formed in a method in which a photocurable resin or a thermoplastic resin is pressed with a nano-imprint mold, i.e., a mold having concave portions each having a nanometer size, being irradiated with light and heated, to transfer a pattern of the concave portions.

(Reflective Sensing System)

FIG. 7 shows a configuration of a sensing system 40 of a reflective optical arrangement according to an embodiment of the present invention. The sensing system 40 includes a light source 42, a collimator lens 44, a stray light removing plate 46, a beam splitter 48, the sensing chip 10, and a photodetector 50. Note that the sensing chip 20 may be used in place of the sensing chip 10 and a half mirror may be used in place of the beam splitter 48. The sensing system 40 is a system which quantitatively evaluates the adsorption of a detection substance (e.g., a specific protein, virus, or hormone) which can be contained in a test sample (e.g., saliva, blood, urine, or body fluid) after having the test sample applied to the sensing chip 10. Therefore, using the sensing system 40 can make it possible to determine whether a detection substance is adsorbed to the sensing chip 10.

The light source 42 is preferably the one which emits white light such as a halogen lamp or LED but may be any type of light source which emits light including a wavelength region used for detection. The light source 42 irradiates the sensing chip 10 with light. That is, light emitted from the light source 42 is guided to the collimator lens 44. Light passing through the collimator lens 44 becomes parallel light and is guided to the stray light removing plate 46. Parallel light passing through a pinhole of the stray light removing plate 46 is guided to the beam splitter 48. About ½ amount of the parallel light entering the beam splitter 48 linearly passes through the beam splitter 48 and irradiates the sensing chip 10.

The parallel light with which the sensing chip 10 is irradiated is reflected by the sensing chip 10 and returns as measurement light to the original direction. The measurement light returning in the original direction enters the beam splitter 48. About ½ amount of the measurement light entering the beam splitter 48 is reflected by a joined surface inside the beam splitter 48, with the entered measurement light being bent at 90° of the traveling direction. The photodetector 50 receives the measurement light reflected by the beam splitter 48. That is, the photodetector 50 detects the optical spectrum of light emitted from the light source 42 and then reflected in the detection region of the sensing chip 10. The photodetector 50 includes a spectrometer unit, a photodetection unit, and a data processing unit. The spectrometer unit splits the measurement light received by the photodetector 50 into the respective wavelengths. The photodetection unit detects intensity of light of each wavelength. The data processing unit processes this detected data.

Note that the data processing unit of the photodetector 50 has been provided in advance with data of the optical spectrum of measurement light reflected in the detection region of the sensing chip 10 to which no detection substance is adsorbed. For example, the optical spectrum of measurement light reflected in the detection region of the sensing chip 10 is measured immediately before a test sample is applied to the sensing chip 10, and the measurement result can be obtained as data without any detection substance adsorbed to the chip. The data processing unit then quantitatively evaluates adsorption of the detection substance to the sensing chip 10 by comparing the data without any detection substance adsorbed to the chip with the data of the optical spectrum of the measurement light reflected in the detection region of the sensing chip 10. The data processing unit incorporates software which can perform this comparison and evaluation. That is, the data processing unit can also determine whether a detection substance is adsorbed to the sensing chip 10.

In addition, the sensing system 40 may further include a wireless communication device 52 and a portable terminal 54. In this case, a data processing unit (CPU) of the portable terminal 54 quantitatively evaluates the adsorption of a detection substance to the sensing chip 10 by the following method, in place of the data processing unit of the photodetector 50. That is, the wireless communication device 52 wirelessly transmits the data of the optical spectrum detected by the photodetector 50. When performing wireless transmission, it is possible to use a cellular phone wireless communication technology (e.g., LTE® or 3G), wireless LAN (e.g., Wi-Fi), or near field communication (e.g., Bluetooth®). The portable terminal 54 receives data wirelessly transmitted from the wireless communication device 52 and quantitatively evaluates the adsorption of a detection substance to the sensing chip 10 based on this data.

The portable terminal 54 to be used can be a cellular phone, a smartphone, a tablet, a notebook personal computer, or the like. The portable terminal 54 has been provided in advance with data of the optical spectrum of measurement light reflected in the detection region of the sensing chip 10 to which no detection substance is adsorbed. For example, the optical spectrum of measurement light reflected in the detection region of the sensing chip 10 is measured immediately before a test sample is applied to the sensing chip 10, and the portable terminal 54 can receive the measurement result as data without any detection substance adsorbed to the chip. The portable terminal 54 then wirelessly receives the data of the optical spectrum measured after the test sample is applied to the sensing chip 10, and the data processing unit compares this data with the data without any detection substance adsorbed to the chip, thereby quantitatively evaluating the adsorption of the detection substance to the sensing chip 10.

(Transmissive Sensing System)

FIG. 8 shows a configuration of a sensing system 60 of a transmissive optical arrangement according to an embodiment of the present invention. The sensing system 60 includes a light source 42, a collimator lens 44, a stray light removing plate 46, a sensing chip 10, and a photodetector 50. Note that a sensing chip 20 may be used in place of the sensing chip 10. The sensing system 60 is a system which quantitatively evaluates adsorption of a detection substance which may be contained in a test sample after having the test sample applied to the sensing chip 10.

Light emitted from the light source 42 passes through the collimator lens 44 to become parallel light, and passes through a pinhole of the stray light removing plate 46 to be narrowed down. The light then irradiates the sensing chip 10. A parallel light with which the sensing chip 10 is irradiated is transmitted through the sensing chip 10 and received by the photodetector 50. Like the sensing system 40, a data processing unit of the photodetector 50 has been provided in advance with the data of the optical spectrum of measurement light transmitted through the detection region of the sensing chip 10 to which no detection substance is adsorbed.

For this reason, the data processing unit compares this data with the data of the optical spectrum of the measurement light transmitted through the detection region of the sensing chip 10, thereby quantitatively evaluating the adsorption of the detection substance to the sensing chip 10. In addition, like the sensing system 40, the sensing system 60 may further include a wireless communication device 52 and a portable terminal 54. The sensing system 60 including the wireless communication device 52 and the portable terminal 54, in the same manner as the sensing system 40 including them, quantitatively evaluates the adsorption of the detection substance to the sensing chip 10.

(Portable Sensing System)

FIG. 9 shows a configuration of a portable sensing system 70 according to an embodiment of the present invention. The sensing system 70 includes a measurement device 72, an analyzer 74, and a data storage device 76. In this embodiment, the measurement device 72 has a transmissive optical arrangement but may have a reflective optical arrangement. The measurement device 72 includes a light source 42, a collimator lens 44, a stray light removing plate 46, and a chip holder 77. The chip holder 77 holds a sensing chip 10. The chip holder 77 may hold a sensing chip 20 in place of the sensing chip 10. The sensing system 70 is a system which quantitatively evaluates adsorption of a detection substance which may be contained in a test sample after having the test sample applied to the sensing chip 10.

The analyzer 74 includes a shooting unit 78 as a shooting device, an evaluation unit 80 as an evaluation device, and a wireless communication unit 82 as a wireless communication device. In this embodiment, a smartphone is used as the analyzer 74. A cellular phone, a tablet, a notebook personal computer, or the like, other than a smartphone, can be used as the analyzer 74. In this embodiment, a shooting device, an evaluation device, a wireless communication device, and the like are integrally formed as the analyzer 74. However, these devices may be discrete and independent. For example, separately providing an evaluation device and a wireless communication device allows a digital camera to be used as a shooting device.

The shooting unit 78 shoots the detection region of the sensing chip 10 by using a built-in camera of the smartphone. That is, when a reflective system is used, the shooting unit 78 shoots a surface of the detection region on which incident light is reflected, and when a transmissive system is used, the shooting unit 78 shoots a surface of the detection region through and from which incident light is transmitted and emitted. The evaluation unit 80 quantitatively evaluates the adsorption of a detection substance to the sensing chip 10 based on chromaticity of an image of the detection region shot by the shooting unit 78. The evaluation unit 80 has been provided in advance with data of chromaticity obtained by shooting the detection region of the sensing chip 10 to which no detection substance adheres. For example, in this system, the detection region of the sensing chip 10 is shot immediately before a test sample is applied to the sensing chip 10, and the resultant chromaticity data can be used as data without the adsorption of any detection substance.

Then, the evaluation unit 80 which is a CPU of the smartphone compares this data with the chromaticity data of the image of the detection region shot by the shooting unit 78 and quantitatively evaluates the adsorption of the detection substance to the sensing chip 10. The smartphone incorporates software which can perform these comparison and evaluation. When the sensing system 70 includes the measurement device 72, a shooting device, and an evaluation device, the adsorption of a detection substance to the sensing chip 10 can be quantitatively evaluated, even if the sensing system 70 does not include any wireless communication device. The sensing chips 10 and 20 can detect a peak wavelength shift of an optical spectrum before and after the adsorption of a detection substance with high accuracy, and hence, an adsorption amount of the detection substance can be evaluated based on a chromaticity difference. As described above, since the sensing system 70 uses no large-scale apparatus such as a spectrophotometer, the system is easy to carry around and can be used in various situations such as when testing infectious diseases at an edge of water such as an airport and a seaport and being used in a clinical site in a developing country.

Like this embodiment, the sensing system 70 including a wireless communication device will provide more convenience. That is, it is possible to transmit various types of measurement and evaluation data to the data storage device 76 such as a remote server by using the wireless communication device of the sensing system 70. More specifically, the wireless communication unit 82 transmits, to the data storage device 76, at least one of the following data: the chromaticity data of the image of the detection region shot by the shooting unit 78, and the data obtained by quantitatively evaluating the adsorption of a detection substance to the sensing chip 10, i.e., the data of the adsorption amount of the detection substance. Since data can be quickly transmitted in this manner, this system can be used in a wide variety of situations such as situations using an electronic health record system, a remote medical care system, and medical diagnosis and medical examination services.

Note that data to be wirelessly transmitted to the data storage device 76 include, in addition to the above data, (1) an individual identification number of a test sample, (2) a name of a person who performs measurement, (3) test items, (4) test date and time, (5) optical spectrum data, chromaticity data, spectrum peak wavelengths, spectral shift amounts, or chromaticity change amounts before and after adsorption of a detection substance to the sensing chip, and (6) diagnosis determination results such as a positive result, a quasi-positive result, a quasi-negative result, and a negative result. In addition, in the sensing system 70, a widely available smartphone or the like can be used, and hence, bringing the measurement device 72 to a test site makes it possible to detect a detection substance also by using a smartphone or the like possessed by a test object person.

The sensing system 70 is used as follows. First, the sensing chip 10 to which a test sample is not applied is held on the chip holder 77. The sensing chip 10 is then irradiated with light from the light source 42, and the surface of the detection region from which the transmitted measurement light emits is shot by the smartphone. In this case, the chromaticity data of the shot image is stored in the smartphone. The sensing chip 10 is then removed from the chip holder 77, and a test sample is applied to the sensing chip 10. Next, this sensing chip 10 is held on the chip holder 77 and is irradiated with light from the light source 42, and the surface of the detection region from which the transmitted measurement light emits is shot by the smartphone. In this system, then, a detection substance contained in the test sample is quantitatively evaluated by comparing the chromaticity data of the image before the test sample is applied with the chromaticity data of the image after the test sample is applied.

EXAMPLE (Refractive Index Response Sensitivity of Sensing Chip)

Absorbance of light transmitted through a sensing chip having a stretching degree $L/L_0$ (corresponding to A/B in FIG. 3) of 1.2 before the formation of a metal layer on its front surface in each type of mediums was measured. A tabletop spectrophotometer (U-1900 manufactured by Hitachi High-Technologies Corporation) was used to measure absorbance spectra. FIG. 10 shows these optical spectra. When a refractive index n of the detection region surface of the sensing chip changed, the peak wavelength of an optical spectrum also greatly changed. FIG. 11 shows a relation between a refractive index n of a medium present on the detection region surface of the sensing chip and a peak wavelength of an optical spectrum. The refractive index response sensitivity being the gradient of the plot in FIG. 11 was about 440, which was twice or more the refractive index response sensitivity of the chip described in International Publication No. WO 2011/121857. These results revealed that the sensing chip according to the present invention had high sensitivity.

(Concentration Dependence and Lower Detection Limit Concentration of Influenza Virus Detection of Sensing Chip)

(1) Manufacture of Sensing Chip

A sensing chip 20 having a stretching degree $L/L_0$ of 1.2 was manufactured by the above method. The uppermost front surface of the sensing chip 20 is a thin gold film having a thickness of 100 nm and formed by the vacuum deposition. Then, an organic molecular layer for fixing biomolecules was further formed on the front surface of the thin gold film of the sensing chip 20 in accordance with the following procedure. First, the detection region of the sensing chip 20 was cleaned by sequentially applying ethanol and a phosphate buffer solution (200 mmol/L, pH 7.4) in increments of 1 mL.

Next, an antibody layer was formed on the front surface of the sensing chip 20. That is, a phosphate buffer solution of an antibody (influenza A virus nucleoprotein recognizing antibody manufactured by Bio Matrix Inc.) with a concentration of 10 µg/mL was dropped onto the cleaned sensing chip by 150 µL to 200 µL and left to stand for an hour. Thereafter, the resultant structure was rinsed with a phosphate buffer solution and dried by blowing a dry air. Then, the antibody surface was covered with a blocking agent to suppress adhesion of a substance other than a detection substance. That is, a phosphate buffer solution of BSA (Cohn Fraction V manufactured by Wako Pure Chemical Industries, Ltd., pH 7.0) with a concentration of 1 µg/mL was dropped onto the sensing chip after the formation of the antibody by 150 µL to 200 µL and left to stand for 30 minutes. Thereafter, the resultant structure was rinsed with a phosphate buffer solution and dried by blowing a dry air.

(2) Detection of Influenza Virus

The detection performance of the sensing chip obtained in this manner was evaluated. First, an antigen (influenza A virus (A/Solomon Islands/2006(H1N1))) was diluted with a phosphate buffer solution to prepare 10-fold dilution series solutions with a concentration of 15 pg/mL to 15 µg/mL. Next, solutions with various concentrations were sequentially applied to the same sensing chip for 15 minutes, starting from a low-concentration solution. Absorbance of light transmitted through the sensing chip was measured at each concentration. FIG. 12 shows a relation between an antigen concentration of each solution applied to the sensing chip and each peak wavelength (absorption maximum wavelength) of optical spectra.

As shown in FIG. 12, with this sensing chip, as the antigen concentration increased by 10 times, the peak wavelength of the corresponding optical spectrum changed by about 1 nm. In addition, with the sensing chip, an antigen was able to be detected from even a solution with an antigen concentration of 1.5 ng/mL. A commercially available influenza test kit (immunochromatography kit) has a lower detection limit concentration of 50 ng/mL to 100 ng/mL. Accordingly, it became clear that the sensing chip according to the present invention was able to detect influenza virus even if the influenza virus concentration is several ten times lower than the lower influenza virus concentration limit that is able to be detected by the commercially available product.

(Relation Between Surface Structures and Optical Spectra)

The optical spectra of measurement light reflected by the sensing chips 10 each having a different surface structure were calculated by simulations using an FDTD simulator. The simulations were performed by setting the thickness of the uppermost front surface of each thin gold film to 100 nm, the diameter D of the divided surface as the bottom surface of each protruding portion to 500 nm, and the height H of each protruding portion to 0 nm to 200 nm. FIG. 13 shows optical spectra for the respective heights of protruding portions. Although the absorption peak caused by localized surface plasmon resonance decreased with a decrease in height, an absorption peak was confirmed when the height H was 50 nm or more.

In addition, protruding portions 16 of the sensing chips 10 and protruding portions of the sensing chip according to the third embodiment were formed by using imprint molds. That is, four types of the sensing chips 10 with the dimeter D of each divided surface as the bottom surface of each protruding portion being 500 nm and the heights H of the respective protruding portions being 164 nm, 193 nm, 222 nm, and 254 nm, which were the sensing chips according to the first embodiment (H: 164 nm, 193 nm, and 222 nm) and the sensing chip according to the third embodiment (H: 254 nm), were manufactured. The optical spectra of measurement light reflected by these sensing chips were measured. FIG. 14 shows optical spectra for the respective heights of the producing portions. Although the absorption peak caused by localized surface plasmon resonance decreased with an increase in height, absorption peaks were able to be confirmed at all the heights. With the three types of sensing chips with the heights H being 164 nm, 193 nm, and 222 nm, in particular, clear absorption peaks were confirmed.

As described above, when the height H is equal to or more than 50 nm and less than 250 nm, i.e., the ratio H/D is equal to or more than 0.1 and less than 0.5, adsorption of a detection substance can be quantitatively evaluated. A sensing chip is particularly preferred, which includes protruding portions with the height H being 50 nm to 222 nm, i.e., the ratio H/D being 0.1 to 0.444. Note that, even by using the sensing chip 20, it seems possible to quantitatively evaluate the adsorption of a detection substance when the ratio H/A of the height H of each protruding portion to the length A of each divided surface in the longitudinal direction is equal to or more than 0.1 and less than 0.5.

The optical spectra of measurement light reflected by sensing chips having different surface structures according to the third embodiment were calculated by simulations using the FDTD simulator. The simulations were performed by setting the thickness of the uppermost front surface of each thin gold film to 100 nm, the diameter D of the divided surface as the bottom surface of each protruding portion to 500 nm, and the height H of each protruding portion to 1,500 nm to 5,000 nm. FIG. 15 shows optical spectra for the respective heights of protruding portions. With any of the sensing chips with the heights H being 1,500 nm to 5,000 nm, an absorbance peak was present. Although the protruding portions of each sensing chip according to the third embodiment is fabricated by using a microfabrication technique such as lithography or nano-imprinting, the practical height H is 3,000 nm or less in consideration of the process limitation where the ratio H/D is about 5.

In addition, although not shown, when the heights H were 500 nm to 1,000 nm, the optical spectra showed complicated patterns and high absorbances, and the peaks of optical absorption spectra became dull. However, with any of the sensing chips with the heights H being 500 nm to 1,000 nm, an absorbance peak was present. Moreover, as shown in FIG. 14, even with the sensing chip with the height H being 254 nm, an absorbance peak was present.

As described above, when the height H is more than 250 nm and equal to or less than 3,000 nm, i.e., the ratio H/D is more than 0.5 and equal to or less than 6, it is possible to obtain a practical sensing chip which can quantitatively evaluate adsorption of a detection substance. A sensing chip is especially preferred, which includes protruding portions with the height H being 254 nm to 3,000 nm, i.e., the ratio H/D being 0.508 to 6. Note that, even by using the sensing chip according to the fourth embodiment, it seems possible to quantitatively evaluate the adsorption of a detection substance when the ratio H/A of the height H of each protruding portion to the length A of each divided surface in the longitudinal direction is more than 0.5 and equal to or less than 6. In addition, the sensing chips according to the third and fourth embodiments can be used for the reflective sensing system, the transmissive sensing system, the portable sensing system, and the like according to the embodiments.

The sensing chip and the sensing system according to the present invention can be suitably used for high-sensitivity biosensors and the like.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A localized surface plasmon resonance sensing chip comprising:
    a base having a flat-plate shape;
    a plurality of protruding portions each having a shape like a semi-oblate spheroid which is one of three-dimensional parts obtained by dividing an oblate spheroid in half along an equatorial plane and arranged such that a divided surface of the semi-oblate spheroid faces a front surface of the base; and
    a metal layer covering each front surface of the plurality of protruding portions,
    wherein the plurality of protruding portions are arranged at predetermined pitches in a diametrical direction of the divided surface and a direction perpendicular to the diametrical direction, respectively.

2. The localized surface plasmon resonance sensing chip according to claim 1,
    wherein a ratio H/D of a height H of the protruding portion to a diameter D of the divided surface is not less than 0.1 and less than 0.5.

3. The localized surface plasmon resonance sensing chip according to claim 1,
    wherein a thickness of the metal layer is 10 nm to 200 nm.

4. The localized surface plasmon resonance sensing chip according to claim 1,
    wherein each of the pitches is 100 nm to 3,000 nm.

5. The localized surface plasmon resonance sensing chip according to claim 1,
    wherein the metal layer is made of Au, Pt, Ag, Al, or an alloy thereof.

6. The localized surface plasmon resonance sensing chip according to claim 1, wherein the plurality of protruding portions are closely packed.

7. The localized surface plasmon resonance sensing system according to claim 1, comprising:
   a light source irradiating a detection region of the localized surface plasmon resonance sensing chip with light; and
   a photodetector detecting an optical spectrum of light emitted from the light source and then reflected in or transmitted through the detection region of the localized surface plasmon resonance sensing chip.

8. The localized surface plasmon resonance sensing system according to claim 7, further comprising:
   a wireless communication device wirelessly transmitting data of an optical spectrum detected by the photodetector; and
   a portable terminal receiving the data wirelessly transmitted from the wireless communication device and quantitatively evaluating adsorption of a detection substance to the localized surface plasmon resonance sensing chip based on the data.

9. The localized surface plasmon resonance sensing system according to claim 1, comprising:
   a light source irradiating a detection region of the localized surface plasmon resonance sensing chip with light;
   a shooting device shooting the detection region of the localized surface plasmon resonance sensing chip; and
   an evaluation device quantitatively evaluating adsorption of a detection substance to the localized surface plasmon resonance sensing chip based on chromaticity of an image of the detection region shot by the shooting device.

10. A localized surface plasmon resonance sensing chip comprising:
    a base having a flat-plate shape;
    a plurality of protruding portions each having a shape like a semi-prolate spheroid which is one of three-dimensional parts obtained by dividing a prolate spheroid in half along a direction perpendicular to an equatorial plane and arranged such that a divided surface of the semi-prolate spheroid faces a front surface of the base; and
    a metal layer covering each front surface of the plurality of protruding portions,
    wherein the plurality of protruding portions are arranged at predetermined pitches in a longitudinal direction of the divided surface and a direction perpendicular to the longitudinal direction, respectively, with longitudinal directions of the divided surfaces being parallel to each other.

11. The localized surface plasmon resonance sensing chip according to claim 10,
    wherein a ratio H/A of a height H of the protruding portion to a length A of the divided surface in the longitudinal direction is not less than 0.1 and less than 0.5.

12. The localized surface plasmon resonance sensing chip according to claim 10,
    wherein a thickness of the metal layer is 10 nm to 200 nm.

13. The localized surface plasmon resonance sensing chip according to claim 10,
    wherein each of the pitches is 100 nm to 3,000 nm.

14. The localized surface plasmon resonance sensing chip according to claim 10,
    wherein the metal layer is made of Au, Pt, Ag, Al, or an alloy thereof.

15. The localized surface plasmon resonance sensing chip according to claim 10,
    wherein the plurality of protruding portions are closely packed.

16. The localized surface plasmon resonance sensing system according to claim 10, comprising:
    a light source irradiating a detection region of the localized surface plasmon resonance sensing chip with light; and
    a photodetector detecting an optical spectrum of light emitted from the light source and then reflected in or transmitted through the detection region of the localized surface plasmon resonance sensing chip.

17. The localized surface plasmon resonance sensing system according to claim 16, further comprising:
    a wireless communication device wirelessly transmitting data of an optical spectrum detected by the photodetector; and
    a portable terminal receiving the data wirelessly transmitted from the wireless communication device and quantitatively evaluating adsorption of a detection substance to the localized surface plasmon resonance sensing chip based on the data.

18. The localized surface plasmon resonance sensing system according claim 10, comprising:
    a light source irradiating a detection region of the localized surface plasmon resonance sensing chip with light;
    a shooting device shooting the detection region of the localized surface plasmon resonance sensing chip; and
    an evaluation device quantitatively evaluating adsorption of a detection substance to the localized surface plasmon resonance sensing chip based on chromaticity of an image of the detection region shot by the shooting device.

19. A localized surface plasmon resonance sensing chip comprising:
    a base having a flat-plate shape;
    a plurality of protruding portions each having a shape like one of three-dimensional parts obtained by dividing a prolate spheroid in half along an equatorial plane and arranged such that a divided surface of the three-dimensional part faces a front surface of the base; and
    a metal layer covering each front surface of the plurality of protruding portions,
    wherein the plurality of protruding portions are arranged at predetermined pitches in a diametrical direction of the divided surface and a direction perpendicular to the diametrical direction, respectively.

20. The localized surface plasmon resonance sensing chip according to claim 19,
    wherein a ratio H/D of a height H of the protruding portion to a diameter D of the divided surface is more than 0.5 and not more than 6.

* * * * *